US009259410B2

(12) United States Patent
Schutz

(10) Patent No.: US 9,259,410 B2
(45) Date of Patent: Feb. 16, 2016

(54) METHODS OF TREATING POLYCYSTIC OVARIAN SYNDROME USING CHLOROGENIC ACID AND INOSITOL

(71) Applicant: Oculus Innovative Sciences, Inc., Petaluma, CA (US)

(72) Inventor: James J. Schutz, Petaluma, CA (US)

(73) Assignee: Oculus Innovative Sciences, Inc., Petaluma, CA (US)

( * ) Notice: Subject to any disclaimer, the term of this patent is extended or adjusted under 35 U.S.C. 154(b) by 0 days.

(21) Appl. No.: 14/248,064

(22) Filed: Apr. 8, 2014

(65) Prior Publication Data

US 2015/0283107 A1 Oct. 8, 2015

(51) Int. Cl.
*A61K 31/216* (2006.01)
*A61K 31/047* (2006.01)
*A61K 36/185* (2006.01)
*A61K 31/198* (2006.01)

(52) U.S. Cl.
CPC ............. *A61K 31/216* (2013.01); *A61K 31/047* (2013.01); *A61K 31/198* (2013.01); *A61K 36/185* (2013.01)

(58) Field of Classification Search
None
See application file for complete search history.

(56) References Cited

U.S. PATENT DOCUMENTS

| | | | | |
|---|---|---|---|---|
| 5,906,979 | A * | 5/1999 | Allan | 514/25 |
| 8,372,447 | B2 * | 2/2013 | Doherty et al. | 424/725 |
| 2002/0054923 | A1 | 5/2002 | Suzuki et al. | |
| 2003/0091690 | A1 | 5/2003 | Somoto et al. | |
| 2007/0178216 | A1 * | 8/2007 | Kandaswami et al. | 426/597 |
| 2010/0105691 | A1 | 4/2010 | Yie et al. | |
| 2010/0112101 | A1 | 5/2010 | Gokaraju et al. | |
| 2010/0215782 | A1 | 8/2010 | Babish et al. | |
| 2010/0323033 | A1 | 12/2010 | Kim et al. | |
| 2011/0015140 | A1 | 1/2011 | Andary et al. | |
| 2011/0052718 | A1 | 3/2011 | Rangel | |
| 2014/0045937 | A1 | 2/2014 | Schutz | |

FOREIGN PATENT DOCUMENTS

| | | |
|---|---|---|
| CN | 102526015 A | 7/2012 |
| WO | WO 2012/080273 A1 * | 6/2012 |
| WO | WO 2014/025864 A2 | 2/2014 |

OTHER PUBLICATIONS

Ohnuki et al., "Effects of L-cysteine on blood pressure in hypertensive rats and some aspects of its mechanism," *Yakuri to Chiryo*, 15:1195-1201 (1987).
Banihani et al., "Pomegranate and type 2 diabetes," *Nutr. Res.*, 33, 341-8 (2013).
Carlomagno et al., "Inositol safety: clinical evidences," *Eur. Rev. Pharmacol. Sci.*, 15, 931-6 (2011).
Croze et al., "Potential role and therapeutic interests of myo-inositol in metabolic diseases," *Biochimie.*, 95, 1811-27 (2013).
Galletta et al., "Bye-bye chiro-inositol—myo-inositol: true progress in the treatment of polycystic ovary syndrome and ovulation induction," *Eur. Rev. Med. Pharmacol. Sci.*, 15, 1212-4 (2011).
Genazzani et al., "Differential insulin response to myo-inositol administration in obese polycystic ovary syndrome patients," *Gynecol. Endocrinol.*, 28, 969-73 (2012).
Genazzani et al., "Myo-inositol modulates insulin and luteinizing hormone secretion in normal weight patients with polycystic ovary syndrome," *J. Obstet. Gynaecol., Res.*, (2014).
Gerli et al., "Randomized, double blind placebo-controlled trial: effects of myo-inositol on ovarian function and metabolic factors in women with PCOS," *Eur. Rev. Med. Pharmacol. Sci.*, 11, 347-54 (2007).
Jakimiuk et al., "The role of inositol deficiency in the etiology of polycystic ovary syndrome disorders," *Ginekol. Pol.*, 85, 54-7 (2014).
Johanningsmeier et al., "Pomegranate as a functional food and nutraceutical source," *Annu. Rev. Food Sci. Technol.*, 2, 181-201 (2011).
Macut et al., "Dyslipidemia and oxidative stress in PCOS," *Front Horm. Res.*, 40, 51-63 (2013).
Medjakovic et al., "Pomegranate: a fruit that ameliorates metabolic syndrome," *Food Funct.*, 4, 19-39 (2013).
Papaleo et al., "Contribution of myo-inositol to reproduction," *Eur. J. Obstet. Gynecol. Reproduc. Biol.*, 147, 120-3 (2009).
Pizzo et al., "Comparison between effects of myo-inositol and D-chiro-inositol on ovarian function and metabolic factors in women with PCOS," *Gynecol. Endocrinol.*, 30, 205-8 (2014).
Rushworth et al., "Existing and potential therapeutic uses for N-acetylcysteine: the need for conversion to intracellular glutathione for antioxidant benefits," *Pharmacol. Ther.*, 141, 150-9 (2014).
Sueishi et al., "Scavenging rate constants of hydrophilic antioxidants against multiple reactive oxygen species," *J. Clin. Biochem. Nutr.*, 54, 67-74 (2014).
Artini et al., "Endocrine and clinical effects of myo-inositol administration in polycystic ovary syndrome. A randomized study," *Gynecol. Endocrinol.*, 29(4), 375-9 (2013).
Azziz et al., "The prevalence and features of the polycystic ovary syndrome in an unselected population," *J. Clin. Endocrinol. Metab.*, 89(6), 2745-9 (2004).
Ciotta et al., "Effects of myo-inositol supplementation on oocyte's quality in PCOS patients: a double blind trial," *Eur. Rev. Med. Pharmacol Sci.*, 15, 509-14 (2011).
Dona et al., "Inositol administration reduces oxidative stress in erythrocytes of patients with polycystic ovary syndrome," *European Journal of Endocrinol.*, 166, 703-10 (2012).
Fulghesu et al., "N-acetyl-cysteine treatment improves insulin sensitivity in women with polycystic ovary syndrome," *Fertil. Steril.*, 77(6), 1128-35 (2002).
Gerli et al., "Effects of inositol on ovarian function and metabolic factors in women with PCOS: a randomized double blind placebo-controlled trial," *Eur. Rev. Med. Pharmacol. Sci.*, 7, 151-9 (2003).
Hashim et al., "N-acetyl cysteine plus clomiphene citrate versus metformin and clomiphene citrate in treatment of clomiphene-resistant polycystic ovary syndrome: a randomized controlled trial," *J. Womens Health (Larchmt)*, 19(11), 2043-8 (2010).

(Continued)

*Primary Examiner* — Susan Hoffman
(74) *Attorney, Agent, or Firm* — Leydig, Voit & Mayer, Ltd.

(57) ABSTRACT

The invention provides a method of treating or preventing polycystic ovarian syndrome (PCOS) in a mammal, comprising administering chlorogenic acid and inositol in an amount effective to treat or prevent PCOS in the mammal. In an embodiment of the invention, the method further comprises administering L-cysteine to the mammal.

15 Claims, No Drawings

(56) References Cited

OTHER PUBLICATIONS

Kim et al., "HemoHIM improves ovarian morphology and decreases expression of nerve growth factor in rats with steroid-induced polycystic ovaries," *Journal of Medicinal Food*, 12(6), 1348-52 (2009).

Le Donne et al., "Diet, metformin and inositol in overweight and obese women with polycystic ovary Syndrome: effects on body composition," *Minerva Ginecol.*, 64(1), 23-9 (2012).

Litrel et al., "Evaluation of Glucorein PCOS on Ovulation and Conception in Anovulatory Women with Polycystic Ovary Syndrome," *White Paper*. (2013).

Masha et al., "Prolonged treatment with N-acetylcysteine and L-arginine restores gonadal function in patients with polycystic ovary syndrome," *J. Endocrinol. Invest.*, 32(11), 870-2 (2009).

Nasr, "Effect of N-acetyl-cysteine after ovarian drilling in clomiphene citrate-resistant PCOS women: a pilot study," *Reprod. Biomed. Online*, 20(3), 403-9 (2010).

Oner et al., "Clinical, endocrine and metabolic effects of metformin vs N-acetyl-cysteine in women with polycystic ovary syndrome," *Eur. J. Obstet. Gynecol. Reprod. Biol.*, 159(1), 127-31 (2011).

Palomba et al., "Management strategies for ovulation induction in women with polycystic ovary syndrome and known clomifene citrate resistance." *Curr. Opin. Obstet. Gynecol.*, 21(6), 465-73 (2009).

Papaleo et al., "Myo-inositol in patients with polycystic ovary syndrome: a novel method for ovulation induction," *Gynecol. Endocrinol.*, 23, 700-3 (2007).

Rizk et al., "N-acetyl-cysteine is a novel adjuvant to clomiphene citrate in clomiphene citrate-resistant patients with polycystic ovary syndrome," *Fertil. Steril.*, 83(2), 367-70 (2005).

Saha et al., "Pharmacotherapy of polycystic ovary syndrome—an update," *Fundam. Clin. Pharmacol.*, 26(1), 54-62 (2012).

Salehpour et al., "N-Acetylcysteine as an adjuvant to clomiphene citrate for successful induction of ovulation in infertile patients with polycystic ovary syndrome," *J. Obstet. Gynaecol. Res.*, 38(9), 1182-6 (2012).

Wehr et al., "Association of hypovitaminosis D with metabolic disturbances in polycystic ovary syndrome," *Eur. J. Endocrinol.*, 161(4), 575-82 (2009).

U.S. Patent & Trademark Office, International Search Report in International Application No. PCT/US2013/053918 (Jan. 10, 2014).

U.S. Patent & Trademark Office, Written Opinion in International Application No. PCT/US2013/053918 (Jan. 10, 2014).

"Glucorein—A New Natural Alternative to Metformin," *The PCOS and Infertility Journey*, http://thepcosandinfertilityjourney.com.wordpress.com/tag/glucorein/ posted May 15, 2012 (3 pgs.).

Ganie et al., "Comparison of Efficacy of Spironolactone with Metformin in the Management of Polycystic Ovary Syndrome: An Oopen-Labeled Study," *Journal of Clinical Endocrinology and Metabolism*, vol. 89, No. 6, pp. 2756-2762 (2004).

GLYCIPHAGE® Product Description, Diabétix, http://diabetix-francoindian.com/glyciphage.html downloaded 2013.

Aiache et al., "Powders as Dosage Forms," *Encyclopedia of Pharmaceutical Technology*, pp. 2971-2982 (2007).

Flanagan et al., "Use of N-acetylcysteine in clinical toxicology," *American Journal of Medicine*, vol. 91, Issue 3, Supplement 3, pp. S131-S139 (1991)—Abstract Only.

* cited by examiner

METHODS OF TREATING POLYCYSTIC OVARIAN SYNDROME USING CHLOROGENIC ACID AND INOSITOL

BACKGROUND OF THE INVENTION

Polycystic ovarian syndrome (PCOS) is a hormonal disorder among women of reproductive age. Patients with PCOS may experience any one or more of infrequent or prolonged menstrual periods, excess hair growth, acne, obesity, and ovarian cysts. Possible complications of PCOS may include any one or more of diabetes, high blood pressure, high cholesterol, endometrial cancer, infertility, and breast cancer.

In spite of considerable research into methods of treating PCOS, there still exists a need for improved methods for treating PCOS.

BRIEF SUMMARY OF THE INVENTION

An embodiment of the invention provides a method of treating or preventing PCOS in a mammal, the method comprising administering chlorogenic acid and inositol in an amount effective to treat or prevent PCOS in the mammal.

Another embodiment of the invention provides a pharmaceutical composition comprising chlorogenic acid, inositol, and a pharmaceutically acceptable carrier.

DETAILED DESCRIPTION OF THE INVENTION

It has been discovered that a combination of chlorogenic acid and inositol treats or prevents PCOS. Accordingly, an embodiment of the invention provides a method of treating or preventing polycystic ovarian syndrome (PCOS) in a mammal, the method comprising administering chlorogenic acid and inositol in an amount effective to treat or prevent PCOS in the mammal.

Chlorogenic acid (also known as 3-caffeoylquinic acid, chlorogenate, 3-O-caffeoylquinic acid, heriguard, and 3-(3,4-dihydroxycinnamoyl)quinic acid) is generally present in the leaves or fruits of dicotyledonous plants (for example, Rosaceae fruits such as apple, pear, peach, coffee bean, cacao bean, seed of grape, and artichoke). Chlorogenic acid may be chemically described as (1S,3R,4R,5R)-3-[(E)-3-(3,4-dihydroxyphenyl)prop-2-enoyl]oxy-1,4,5-trihydroxycyclohexane-1-carboxylic acid. Chlorogenic acid has a molecular formula of $C_{16}H_{18}O_9$, a molecular weight of 354.30872, and has the following chemical structure:

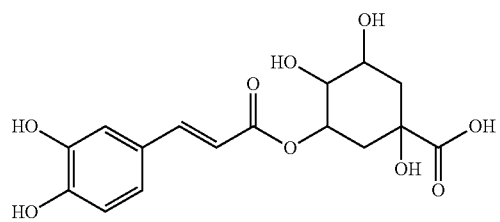 [SMILES: O=C(/C=C/c1ccc(O)c(O)c1)OC1CC(O)(C(=O)O)CC(O)C1O]

Chlorogenic acid may, advantageously, maintain any one or more of healthy blood glucose levels, basal metabolic rates, and resting metabolic rates (e.g., maintenance of glucose levels and metabolic rates already in the normal range). For example, chlorogenic acid may, advantageously, provide any one or more of an anti-diabetic effect, a decrease in insulin resistance, a lessened glycemic peak, stimulation of weight loss by, e.g., boosting metabolism, a lowering of lipids in plasma, and a lowering of lipids in the liver. Without being bound by a particular theory or mechanism, it is believed that chlorogenic acid inhibits enzymatic activity of G6P in the liver, thus reducing hepatic glucose production.

Inositol is a polyol of cycohexane and exists in nine stereoisomers: myo-inositol, scyllo-inositol, muco-inositol, D-chiro-inositol, neo-inositol, L-chiro-inositol, allo-inositol, epi-inositol, and cis-inositol. Inositol has a molecular formula of $C_6H_{12}O_6$, a molecular weight of 180.15588, and may be chemically described as cyclohexane-1,2,3,4,5,6-hexol.

While the inventive methods may comprise administering any of the nine stereoisomers of inositol, preferably the method comprises administering myo-inositol, D-chiro-inositol, or a combination of myo-inositol and D-chiro-inositol. In an especially preferred embodiment, the inositol comprises myo-inositol.

Myo-inositol is a naturally occurring carbohydrate that may be produced in the human body. Myo-inositol may be involved in various functions in the body, including the metabolism of glucose and the regulation of insulin. Myo-inositol may be chemically described as cis-1,2,3,5-trans-4,6-cyclohexanehexol and has the following chemical structure:

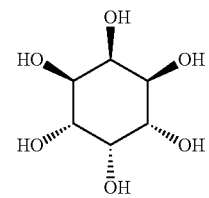 [SMILES: O[C@H]1[C@H](O)[C@H](O)[C@H](O)[C@@H](O)[C@H]1O]

Myo-inositol may, advantageously, reduce any one or more of the following: post-prandial blood glucose, hirsutism, acne, serum triglycerides, blood pressure, fasting serum insulin, fasting serum glucose, homeostasis model assessment-estimated insulin resistance (HOMA-IR), serum testosterone, serum androstenedione, and metabolic syndrome. Alternatively or additionally, myo-inositol may, advantageously, improve any one or more of the following: insulin sensitivity, follicular maturity, oocyte quality, metabolic parameters, hormonal parameters, menstrual cyclicity, fat metabolism in the liver, spontaneous ovulation, oocyte maturation, and ovarian function. Alternatively or additionally, myo-inositol may, advantageously, maintain any one or more of the following: normal metabolism of glucose, structure of body lipids, and proper function of cell membranes. Without being bound by a particular theory or mechanism, it is believed that myo-inositol can affect membrane composition directly, by increasing intracellular phosphoinositide-related signal transduction (PI) components and/or PI-related pathways, and/or indirectly, by modulating the oxidative stress (OS) induced by the inappropriate hyperinsulinemic response linked to insulin resistance (IR).

D-chiro-inositol has the following chemical structure:

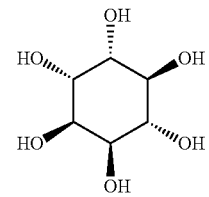

D-chiro-inositol may, advantageously, provide for one or both of insulin regulation and normal metabolism of glucose.

Although in some embodiments the method may comprise administering the chlorogenic acid and the inositol sequentially, preferably the method comprises administering the chlorogenic acid and inositol simultaneously. Although the simultaneous administration of chlorogenic acid and inositol may comprise simultaneously administering a first pharmaceutical composition comprising chlorogenic acid and a second pharmaceutical composition comprising inositol, preferably, the simultaneous administration comprises administering a single pharmaceutical composition comprising both chlorogenic acid and inositol.

The method may comprise administering chlorogenic acid and inositol in an amount effective to treat or prevent PCOS in the mammal. An "effective amount" or "an amount effective to treat" refers to a dose of chlorogenic acid and inositol that is adequate to prevent or treat PCOS. Amounts effective for a therapeutic or prophylactic use will depend on, for example, the stage and severity of the PCOS, the age, weight, and general state of health of the patient, and the judgment of the prescribing physician. The size of the dose will also be determined by the method of administration, timing and frequency of administration, the existence, nature, and extent of any adverse side-effects that might accompany the administration of chlorogenic acid and inositol, and the desired physiological effect. It will be appreciated by one of skill in the art that PCOS could require prolonged treatment involving multiple administrations, perhaps using chlorogenic acid and inositol in each or various rounds of administration. By way of example and not intending to limit the invention, the dose of the chlorogenic acid can be from about 0.2 gram or less to about 1.5 grams or more once, twice, or three or more times per day, preferably from about 0.5 gram to about 1.25 grams once, twice, or three or more times per day, and more preferably about 1 gram once, twice, or three or more times per day. Also by way of example and not intending to limit the invention, the dose of the inositol can be from about 50 mg or less to about 4.0 g or more once, twice, or three or more times per day, or about 200 mg or less to about 4 grams or more once, twice, or three or more times per day, preferably from about 100 mg to about 1.2 gram once, twice, or three or more times per day, or about 600 mg to about 1.2 grams once, twice, or three or more times per day, and more preferably about 200 mg once, twice, or three or more times per day. These doses of inositol may be modified such as, for example, when myo-inositol is combined with other treatments such as, for example, one or both of monacolin K and D-chiro-inositol. In an embodiment of the invention, where the mammal to be treated is an obese female human, any of the doses of chlorogenic acid and inositol described herein (for example, 1 gram of chlorogenic acid and 200 mg of inositol) may be administered multiple times per day (for example, two, three, four, or more times per day.

For purposes of the invention, the amount or dose of the chlorogenic acid and inositol administered should be sufficient to effect a therapeutic or prophylactic response in the mammal over a reasonable time frame. For example, the dose of the chlorogenic acid and inositol should be sufficient treat PCOS in a time period of from about 2 hours or longer, e.g., about 12 to about 24 or more hours, from the time of administration. In certain embodiments, the time period could be even longer. The dose will be determined by the condition of the mammal (e.g., human), as well as the body weight of the mammal (e.g., human) to be treated.

The chlorogenic acid and the inositol may be any suitable chlorogenic acid or inositol, respectively, in any form, and may be obtained in any suitable manner. For example, the chlorogenic acid, inositol, or both may be natural or synthetic. In an embodiment of the invention, administering chlorogenic acid and inositol comprises administering a pharmaceutical composition comprising chlorogenic acid, inositol, and a pharmaceutically acceptable carrier. The pharmaceutical composition comprising chlorogenic acid and inositol may be in any suitable dosage form and may be, for example, solid, semi-solid, gel, or liquid. Preferably, the pharmaceutical composition is in solid form. The pharmaceutical composition may be in any suitable form such as, for example, a powder, pill, tablet, or capsule. Preferably, the pharmaceutical composition is a capsule. The capsule may comprise a hard-shelled capsule or a soft-shelled capsule.

In an embodiment, the soft-shelled capsule may be a soft, globular shell that may be thicker than the shell of hard gelatin capsules. The soft-shell may comprise gelatin. The soft-shell may further comprise plasticizers such as, for example, glycerin, sorbitol, or a similar polyol. These capsules may be sealed at a seam to avoid premature breakage. The shell may further comprise additional components such as, for example, water, titanium dioxide, flavor, sweetener, enteric polymer, non-gelatin film former, and/or dye.

The capsule may have any suitable size. These sizes range from about 000 to about 5 for hard shelled capsules and from about 1 to about 480 for soft shell capsules (also referred to as softgels, soft elastic capsules, or soft gelatin capsules) as described in *Remington: The Science and Practice of Pharmacy*, Lippincott Williams & Wilkins, 19th ed. (1995) (hereinafter Remington's) and *The Theory and Practice of Industrial Pharmacy, Lea & Febiger, Third Edition* (1986). The appropriate capsule size may be readily determined by one of skill in the art depending on the amount and volume of chlorogenic acid and inositol in the composition, e.g. the number of milligrams and volume of chlorogenic acid and inositol in the capsule, to be delivered to the patient.

In an embodiment, the method comprises adding chlorogenic acid and inositol to food and/or beverage for consumption. For example, the method may comprise administering a food and/or beverage comprising chlorogenic acid and inositol. In embodiments in which the chlorogenic acid and inositol are in powder form, the method may comprise mixing and/or dissolving the chlorogenic acid and inositol in a beverage and administering the beverage containing the mixed and/or dissolved chlorogenic acid and inositol to the mammal.

The pharmaceutically acceptable carrier may be any suitable pharmaceutically acceptable carrier. The carrier can be any of those conventionally used and is limited only by chemico-physical considerations, such as solubility and lack of reactivity with the active compound(s), and by the route of administration. The pharmaceutically acceptable carriers described herein, for example, vehicles, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use. The choice of carrier will be determined in part by the particular compounds used in the pharmaceutical composition, as well as by the particular method used to administer the chlorogenic acid and inositol.

In an embodiment of the invention, administering the chlorogenic acid and inositol to the mammal may comprise administering the chlorogenic acid and inositol orally, intravenously, intramuscularly, subcutaneously, or intraperitoneally. The following formulations for oral, intravenous, intramuscular, subcutaneous, or intraperitoneal administration are exemplary and are in no way limiting. More than one route can be used to administer the chlorogenic acid and inositol, and in certain instances, a particular route can provide a more immediate and more effective response than another route.

Oral formulations may include any suitable carrier. For example, formulations suitable for oral administration may comprise suitable carriers, such as lactose, sucrose, starch, talc magnesium stearate, crystalline cellulose, methyl cellulose, carboxymethyl cellulose, glycerin, sodium alginate silica, cellulose, vegetable polysaccharide, or gum arabic among others. In an embodiment, the pharmaceutical composition is a vegetarian pharmaceutical composition. Preferably, the pharmaceutical composition is a vegetarian capsule. In an embodiment of the invention, the pharmaceutical composition does not comprise any one or more of sugar, salt, starch, yeast, wheat, gluten, soy, milk, egg, shellfish, and preservatives. Preferably, the pharmaceutical composition does not comprise all of sugar, salt, starch, yeast, wheat, gluten, soy, milk, egg, shellfish, and preservatives. In an embodiment, the pharmaceutical composition comprises one or more of silica, cellulose, and vegetable polysaccharide. Preferably, the pharmaceutical composition comprises all of silica, cellulose, and vegetable polysaccharide.

In an embodiment of the invention, the carrier for the oral formulation may comprise one or more sweeteners. The sweetener may be any suitable sweetener as is known in the art and may be a natural or non-natural sweetener. Preferably, the sweetener is a natural sweetener. Exemplary sweeteners suitable for use in the present invention include any one or more of sucrose, *stevia*, and aspartame.

In an embodiment of the invention, the carrier for the oral formulation may comprise one or more flavorants. The flavorant may be any suitable flavorant as is known in the art and may be a natural or non-natural flavorant. Preferably, the flavorant is a natural flavorant. Exemplary flavorants suitable for use in the present invention include any one or more of lemon flavorant and cranberry flavorant. In an embodiment of the invention, the flavorant may comprise freeze-dried fruit, e.g., freeze-dried cranberry.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The chlorogenic acid and inositol can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations may comprise preservatives and buffers. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with an embodiment of the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

The pharmaceutical composition may comprise any suitable percentage of chlorogenic acid. In some embodiments, the chlorogenic acid is present in an amount ranging from about 5% or less to about 60% or more by weight of the pharmaceutical composition. In some embodiments, the chlorogenic acid is present in an amount ranging from about 10% to about 55% by weight of the pharmaceutical composition. In some embodiments, the chlorogenic acid is present in an amount ranging from about 15% to about 60% by weight of the pharmaceutical composition. In some embodiments, the chlorogenic acid is present in an amount ranging from about 40% to about 45% by weight of the pharmaceutical composition. Preferably, the chlorogenic acid is present in an amount of about 43% by weight of the pharmaceutical composition.

The pharmaceutical composition may comprise any suitable percentage of inositol. In some embodiments, the inositol is present in an amount ranging from about 1% or less to about 25% or more by weight of the pharmaceutical composition. In some embodiments, the inositol is present in an amount ranging from about 2% to about 20% by weight of the pharmaceutical composition. In some embodiments, the inositol is present in an amount ranging from about 3% to about 15% by weight of the pharmaceutical composition. In some embodiments, the inositol is present in an amount ranging from about 5% to about 10% by weight of the pharmaceutical composition. Preferably, the inositol it present in an amount of about 9% by weight of the pharmaceutical composition.

The pharmaceutical composition comprising chlorogenic acid and inositol may comprise any suitable amount of chlorogenic acid. In some embodiments, the pharmaceutical composition contains an amount of about 100 mg or less to about 1.5 g or more of chlorogenic acid. In some embodiments, the pharmaceutical composition contains an amount of about 200 mg of chlorogenic acid to about 1.25 g of chlorogenic acid. In some embodiments, the pharmaceutical composition contains an amount of about 60 mg to about 500 mg chlorogenic acid. In some embodiments, the pharmaceutical contains about 160 mg to about 400 of chlorogenic acid. In some embodiments, the pharmaceutical composition contains an amount of about 100 mg, about 200 mg, about 300 mg, about 500 mg, about 1 g, about 1.25 g, or about 1.5 g of chlorogenic acid. Preferably, the pharmaceutical composition contains an amount of about 0.3 g of chlorogenic acid (e.g., 333.33 mg or 333 mg).

The pharmaceutical composition comprising chlorogenic acid and inositol may comprise any suitable amount of inositol. In some embodiments, the pharmaceutical composition contains an amount of about 20 mg or less to about 2.0 g or more of inositol. In some embodiments, the pharmaceutical composition contains an amount of about 50 mg to about 1.0 g of inositol. In some embodiments, the pharmaceutical composition contains an amount of about 20 mg to about 1.3 g of inositol. In some embodiments, the pharmaceutical composition contains an amount of about 30 mg to about 400 mg of inositol. In some embodiments, the pharmaceutical composition contains an amount of about 20 mg, about 50 mg, about 60 mg, about 100 mg, about 200 mg, about 300 mg, or about 400 mg of inositol. Preferably, the pharmaceutical composition contains an amount of about 66 mg of inositol (e.g., 66.67 mg or 67 mg).

In an embodiment of the invention, the method may further comprise administering pomegranate extract to the mammal. Pomegranate extract is, advantageously, high in any one or more of dietary fiber, vitamins and antioxidants such as, for example, such as ascorbic acid. Pomegranate extract may, advantageously, reduce any one or more of cholesterol levels, blood pressure, and risk of heart disease. Alternatively or additionally, pomegranate extract may, advantageously, provide one or more of protection against free radical damage, promotion of cell health, support of DNA integrity, reversal of atherosclerotic plaque, anti-cancer effects, immune supporting effects, protection against depression, protection against osteoporosis, and support of cardiovascular health. For example, pomegranate extract may contain phytochemicals called punicalagins that may inhibit abnormal platelet aggregation, thus reducing cardiac risk factors. The method may comprise administering any suitable concentration of pomegranate extract. In an embodiment, the method may comprise administering pomegranate extract in a ratio of about four parts pomegranate and about one part solvent (e.g., ethanol). The method may comprise administering pomegranate extract in any suitable dose. By way of example and not intending to limit the invention, the dose of the pomegranate extract can be from about 25 mg or less to about 1 gram or more once, twice, or three or more times per day, preferably from about 50 mg to about 600 mg once, twice, or three or more times per day, and more preferably about 100 mg once, twice, or three or more times per day.

In an embodiment of the invention, the method further comprises administering cysteine to the mammal. While the cysteine may comprise any suitable cysteine, preferably the cysteine comprises L-cysteine, N-acetyl-L-cysteine (NAC), or a combination of L-cysteine and NAC. In an especially preferred embodiment, the cysteine comprises NAC. Both L-cysteine and NAC are precursors to the antioxidant glutathione (GSH). GSH is a peptide produced in the body that strengthens the immune system and which is composed of glycine, cysteine, and glutamic acid. L-cysteine has antioxidant properties which are typically expressed in GSH. L-Cysteine may be well absorbed in the body and may be converted to GSH quickly. NAC is the acetylated variant of the amino acid L-cysteine and may be used as an alternative source of L-cysteine.

It is believed that L-cysteine may enhance the PCOS therapeutic and/or prophylactic effect achieved by chlorogenic acid. NAC is a synthetic compound derived from L-cysteine. NAC may, advantageously, reduce any one or more of insulin resistance, serum testosterone levels, risk of heart disease, impact of hirusutism, and homocysteine levels. Alternatively or additionally, NAC may provide any one or more of cysteine; improved insulin metabolism; support of normal monthly ovulation; improved insulin sensitivity; support of normal menstrual cycle; maintenance of healthy levels of one or more of estrogen, progesterone, and testosterone; support of the normal expansion and contraction of the endometrial lining; and maintenance of healthy glutathione stores. NAC has been shown to treat or prevent PCOS in a variety of clinical trials as described in, e.g., Fulghesu et al., *Fertil. Steril.*, 77(6): 1128-35 (2002); Salehpour et al., *J. Obstet. Gynaecol. Res.*, e-published ahead of print Apr. 30, 2012; Oner et al., *Eur. J. Obstet. Gynecol. Reprod. Biol.*, 159(1): 127-31 (2011); Saha et al., *Fundam. Clin. Pharmacol.*, 26(1): 54-62 (2012); Hashim et al., *J. Womens Health*, 19(11): 2043-8 (2010); Nasr, *Reprod. Biomed. Online*, 20(3): 403-9 (2009); Masha et al., *J. Endocrinol. Invest.*, 32(11): 870-2 (2009); Rizk et al., *Fertil. Steril.*, 83(2):367-70 (2005); and Fulghesu et al., *Fertil. Steril.*, 77(6): 1128-35 (2002). Without being bound by a particular theory or mechanism, it is believed that NAC alleviates the oxidative stress caused by PCOS by re-establishing the glutathione to ROS equilibrium, thus improving the biochemical parameters of insulin, glucose and testosterone levels.

The cysteine may be any suitable cysteine, in any form, and may be obtained in any suitable manner. The cysteine may be natural or synthetic.

The method may comprise administering any suitable dose of cysteine. A suitable dose of cysteine will depend on, for example, the stage and severity of the PCOS, the age, weight, and general state of health of the patient, and the judgment of the prescribing physician. The size of the dose will also be determined by the method of administration, timing and frequency of administration, the existence, nature, and extent of any adverse side-effects that might accompany the administration of cysteine, and the desired physiological effect. By way of example and not intending to limit the invention, the dose of the cysteine can be from about 250 mg or less to about 1500 mg or more once, twice, or three or more times per day, preferably from about 500 mg to about 1200 mg once, twice, or three or more times per day, and more preferably about 600 mg once, twice, or three or more times per day. In an embodiment of the invention, where the mammal to be treated is an obese female human, any of the doses of cysteine described herein (for example, 600 mg of cysteine) may be administered multiple times per day (for example, two, three, four, or more times per day.

Although in some embodiments the method may comprise administering the chlorogenic acid, the inositol, pomegranate extract, and the cysteine sequentially, preferably the method comprises administering the chlorogenic acid, inositol, pomegranate extract, and cysteine simultaneously. Although the simultaneous administration of chlorogenic acid, inositol, pomegranate extract, and cysteine may comprise simultaneously administering a first pharmaceutical composition comprising chlorogenic acid, a second pharmaceutical composition comprising inositol, a third pharmaceutical composition comprising pomegranate extract, and a fourth pharmaceutical composition comprising cysteine, preferably, the simultaneous administration comprises administering a single pharmaceutical composition comprising all of chlorogenic acid, inositol, pomegranate extract, and cysteine.

Accordingly, in an embodiment of the invention, the method comprises administering a pharmaceutical composition comprising chlorogenic acid, inositol, cysteine, pomegranate extract, and a pharmaceutically acceptable carrier. The pharmaceutical composition comprising chlorogenic acid, inositol, pomegranate extract, and cysteine may be in any suitable dosage form and may be, for example, solid, semi-solid, gel, or liquid. The pharmaceutical composition may be as described herein with respect to other aspects of the invention.

In an embodiment, the method comprises adding chlorogenic acid, inositol, pomegranate extract, and cysteine to food and/or beverage for consumption. For example, the method may comprise administering a food and/or beverage comprising chlorogenic acid, inositol, pomegranate extract, and cysteine. In embodiments in which the chlorogenic acid, inositol, pomegranate extract, and cysteine are in powder form, the method may comprise mixing and/or dissolving the chlorogenic acid, inositol, pomegranate extract, and cysteine in a beverage and administering the beverage containing the mixed and/or dissolved chlorogenic acid, inositol, pomegranate extract, and cysteine to the mammal.

The pharmaceutically acceptable carrier may be any suitable pharmaceutically acceptable carrier, and may be as described herein with respect to other aspects of the invention. The choice of carrier will be determined in part by the particular compounds used in the pharmaceutical composition, as well as by the particular method used to administer the chlorogenic acid, inositol, pomegranate extract, and cysteine.

In an embodiment of the invention, administering the chlorogenic acid, inositol, pomegranate extract, and cysteine to the mammal may comprise administering the chlorogenic acid, inositol, pomegranate extract, and cysteine orally, intravenously, intramuscularly, subcutaneously, or intraperitoneally. Pharmaceutical formulations for oral, intravenous, intramuscular, subcutaneous, or intraperitoneal administration of chlorogenic acid, inositol, pomegranate extract, and cysteine may be as described herein with respect to other aspects of the invention. More than one route can be used to administer the chlorogenic acid, inositol, pomegranate extract, and cysteine, and in certain instances, a particular route can provide a more immediate and more effective response than another route.

The pharmaceutical composition comprising chlorogenic acid, inositol, pomegranate extract, and cysteine may comprise any suitable percentage of cysteine. In some embodiments, the cysteine is present in an amount ranging from about 1% or less to about 50% or more by weight of the pharmaceutical composition. In some embodiments, the cysteine is present in an amount ranging from about 10% to about 40% by weight of the pharmaceutical composition. In some embodiments, the cysteine is present in an amount ranging from about 15% to about 35% by weight of the pharmaceutical composition. In some embodiments, the cysteine is present in an amount ranging from about 20% to about 30% by weight of the pharmaceutical composition. Preferably, the cysteine is present in an amount of about 26% by weight of the pharmaceutical composition.

The pharmaceutical composition comprising chlorogenic acid, inositol, pomegranate extract, and cysteine may comprise any suitable percentage of pomegranate extract. In some embodiments, the pomegranate extract is present in an amount ranging from about 2% or less to about 40% or more by weight of the pharmaceutical composition. In some embodiments, the pomegranate extract is present in an amount ranging from about 5% to about 35% by weight of the pharmaceutical composition. In some embodiments, the pomegranate extract is present in an amount ranging from about 10% to about 30% by weight of the pharmaceutical composition. In some embodiments, the pomegranate extract is present in an amount ranging from about 15% to about 25% by weight of the pharmaceutical composition. Preferably, the pomegranate extract is present in an amount of 22% by weight of the pharmaceutical composition The pharmaceutical composition comprising cysteine, inositol, pomegranate extract, and chlorogenic acid may comprise any suitable amount of cysteine. In some embodiments, the pharmaceutical composition contains an amount of about 100 mg or less to about 1500 mg or more of cysteine. In some embodiments, the pharmaceutical composition contains an amount of about 150 mg of cysteine to about 1200 mg of cysteine. In some embodiments, the pharmaceutical composition contains an amount of about 80 mg to about 500 mg of cysteine. In some embodiments, the pharmaceutical composition contains an amount of about 160 mg to about 400 mg of cysteine. In some embodiments, the pharmaceutical composition contains an amount of about 100 mg, about 200 mg, about 250 mg, about 500 mg, about 600 mg, about 1200 mg, or about 1500 mg of cysteine. Preferably, the pharmaceutical composition contains an amount of about 200 mg of cysteine.

The pharmaceutical composition comprising cysteine, inositol, pomegranate extract, and chlorogenic acid may comprise any suitable amount of pomegranate extract. In some embodiments, the pharmaceutical composition contains an amount of about 50 mg or less to about 1.5 g or more of pomegranate extract. In some embodiments, the pharmaceutical composition contains an amount of about 75 mg to about 1.25 g of pomegranate extract. In some embodiments, the pharmaceutical composition contains an amount of about 100 mg, about 500 mg, about 1 g, about 1.25 g, or about 1.5 g of pomegranate extract. Preferably, the pharmaceutical composition contains an amount of about 100 mg of pomegranate extract.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount or any level of treatment or prevention of a PCOS in a mammal. Furthermore, the treatment or prevention provided by the inventive methods can include treatment or prevention of one or more conditions, complications, or symptoms of PCOS. For example, the inventive methods may provide any one or more of improved ovulatory function, improved regularity of the menstrual cycle, and an improved quality of eggs. Also, for purposes herein, "prevention" can encompass delaying the onset of PCOS, or a symptom, complication, or condition thereof.

The mammal referred to herein can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

An embodiment of the invention provides a pharmaceutical composition comprising chlorogenic acid, inositol, and a pharmaceutically acceptable carrier. In an embodiment, the pharmaceutical composition is an oral pharmaceutical composition.

While the inventive pharmaceutical composition may comprise any of the nine stereoisomers of inositol, preferably the pharmaceutical composition comprises myo-inositol, D-chiro-inositol, or a combination of myo-inositol and D-chiro-inositol, as described herein with respect to other aspects of the invention. In an especially preferred embodiment, the inositol comprises myo-inositol.

In an embodiment, the pharmaceutical composition further comprises cysteine. The cysteine may comprise NAC, L-cysteine, or a combination thereof, as described herein with respect to other aspects of the invention. Preferably the cysteine comprises NAC. In an embodiment, the pharmaceutical composition further comprises pomegranate extract, as described herein with respect to other aspects of the invention.

The pharmaceutical composition may otherwise be as described herein with respect to other aspects of the invention.

EXAMPLE 1

This example demonstrates a pharmaceutical composition comprising chlorogenic acid, NAC, inositol, pomegranate extract, and a pharmaceutically acceptable carrier.

A capsule is prepared including the components set forth in Table 1.

TABLE 1

| Component | Amount |
| --- | --- |
| chlorogenic acid | 333.33 mg |
| NAC | 200 mg |
| myo-inositol | 66.67 mg |
| pomegranate extract | 33.3 mg |

The capsule includes a shell comprising silica, cellulose, and vegetable polysaccharide. One capsule is administered to a human patient three times daily.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating or preventing polycystic ovarian syndrome (PCOS) in a mammal, the method comprising orally administering to the mammal a pharmaceutical composition comprising:
   (i) chlorogenic acid in a daily dose of about 0.2 g to about 1.5 g,
   (ii) cysteine in a daily dose of about 250 mg to about 1500 mg,
   (iii) pomegranate extract in a daily dose of about 25 mg to about 1 g,
   (iv) inositol in a daily dose of about 50 mg to about 4.0 g, and
   (v) a pharmaceutically acceptable carrier,
   to treat or prevent PCOS in the mammal.

2. The method of claim 1, wherein the pharmaceutical composition is a solid pharmaceutical composition.

3. The method of claim 1, wherein the inositol comprises myo-inositol.

4. The method of claim 1, wherein the inositol comprises D-chiro-inositol.

5. The method of claim 1, comprising administering chlorogenic acid in a daily dose of about 0.5 g to about 1.25 g.

6. The method of claim 1, comprising administering chlorogenic acid in a daily dose of about 1 g.

7. The method of claim 1, comprising administering cysteine in a daily dose of about 500 mg to about 1200 mg.

8. The method of claim 1, comprising administering cysteine in a daily dose of about 600 mg.

9. The method of claim 1, wherein the pharmaceutical composition is a capsule.

10. The method of claim 9, wherein the capsule is a vegetarian capsule.

11. The method of claim 1, wherein the cysteine comprises N-acetyl-L-cysteine (NAC), L-cysteine, or a combination thereof.

12. The method of claim 1, wherein the pharmaceutical composition does not comprise any one or more of sugar, salt, starch, yeast, wheat, gluten, soy, milk, egg, shellfish, and preservatives.

13. The method of claim 1, wherein the pharmaceutical composition comprises one or more of silica, cellulose, and vegetable polysaccharide.

14. The method of claim 1, comprising administering inositol in a daily dose of about 100 mg to about 1.2 g.

15. The method of claim 1, comprising administering inositol in a daily dose of about 200 mg.

* * * * *